(12) United States Patent
Freeman

(10) Patent No.: US 11,589,945 B2
(45) Date of Patent: Feb. 28, 2023

(54) SURGICAL RESTRAINT WITH ARM POSITIONING SLING

(71) Applicant: Carl R Freeman, Jacksonville, FL (US)

(72) Inventor: Carl R Freeman, Jacksonville, FL (US)

(73) Assignee: Carl R. Freeman, Jacksonville, FL (US)

( * ) Notice: Subject to any disclaimer, the term of this patent is extended or adjusted under 35 U.S.C. 154(b) by 261 days.

(21) Appl. No.: 16/429,271

(22) Filed: Jun. 3, 2019

(65) Prior Publication Data
US 2019/0365497 A1   Dec. 5, 2019

Related U.S. Application Data

(60) Provisional application No. 62/679,096, filed on Jun. 1, 2018.

(51) Int. Cl.
*A61B 90/14* (2016.01)
*A61F 5/37* (2006.01)

(52) U.S. Cl.
CPC .......... *A61B 90/14* (2016.02); *A61F 5/3738* (2013.01)

(58) Field of Classification Search
CPC ...... A61F 5/00; A61F 5/01; A61F 5/37; A61F 5/3723; A61F 5/3728; A61F 5/373; A61F 5/3761; A61F 5/3769; A61F 5/3776; A61F 5/3874; A61F 5/3746; A61F 5/3738; A61F 5/05808; A61B 90/00; A61B 90/14; A61B 6/04; A61B 6/0407; A61G 13/00; A61G 15/00; A61N 2005/1097

See application file for complete search history.

(56) References Cited

U.S. PATENT DOCUMENTS

| | | | | |
|---|---|---|---|---|
| 3,137,294 A | * | 6/1964 | Robertson | A61F 5/3784 128/874 |
| 3,182,338 A | * | 5/1965 | Shirrod | A61F 5/3784 128/876 |
| 3,474,781 A | * | 10/1969 | Gaylord, Jr. | A61F 5/3784 128/876 |
| 5,358,470 A | * | 10/1994 | Johnson | A61F 5/3746 602/62 |
| 5,413,552 A | * | 5/1995 | Iwuala | A61F 5/3738 602/20 |

(Continued)

*Primary Examiner* — Ophelia A Hawthorne
*Assistant Examiner* — Gina McCarthy
(74) *Attorney, Agent, or Firm* — McNees Wallace & Nurick LLC

(57) ABSTRACT

A surgical restraint is disclosed including a body strap, a sling, and a connecting strap. The body strap is arranged and disposed to wrap over patient's torso and around a support disposed below the patient, restraining the patient against the support. The sling is arranged and disposed to cradle an upper arm, an elbow and a forearm of a patient's arm. The connecting strap includes a first attachment site associated with a brace and a second attachment site associated with the sling. The connecting strap is arranged and disposed to cross over the patient's shoulder between the first attachment site and the second attachment site. The surgical restraint is arranged and disposed to restrain the patient's arm against the patient's torso and removed from a surgical site.

17 Claims, 5 Drawing Sheets

(56) References Cited

U.S. PATENT DOCUMENTS

| | | | | |
|---|---|---|---|---|
| 6,659,971 | B2* | 12/2003 | Gaylord | ............... A61F 5/3738 602/4 |
| 2010/0275377 | A1* | 11/2010 | West | ................... A61G 13/124 5/621 |
| 2011/0192403 | A1* | 8/2011 | Goumas | ............... A61F 5/3738 128/845 |
| 2012/0022417 | A1* | 1/2012 | Thompson | .......... A61F 5/05808 602/4 |
| 2013/0019882 | A1* | 1/2013 | Durham | ............... A61F 5/3776 128/876 |

* cited by examiner

SURGICAL RESTRAINT WITH ARM POSITIONING SLING

RELATED APPLICATIONS

This application claims the benefit of and priority to U.S. Prov. App. No. 62/679,096 entitled "Surgical Restraint with Arm Positioning Sling," filed Jun. 1, 2018, which is hereby incorporated by reference in its entirety.

FIELD OF THE INVENTION

The present invention is directed to a surgical restraint. More particularly, the present invention is directed to a surgical restraint including an arm positioning sling.

BACKGROUND OF THE INVENTION

During certain surgical procedures, a patient's arm's natural resting position may undesirably interfere with the surgical field, or with medical personnel's accessibility thereto. Existing arm slings may not position the arm safely or prevent injury to the patient or prevent interference of the arm during surgery.

BRIEF DESCRIPTION OF THE INVENTION

In an exemplary embodiment, a surgical restraint includes a body strap, a sling, and a connecting strap. The body strap is arranged and disposed to wrap over patient's torso and around a support disposed below the patient, restraining the patient against the support. The sling is arranged and disposed to cradle an upper arm, an elbow and a forearm of a patient's arm. The connecting strap includes a first attachment site associated with a brace and a second attachment site associated with the sling. The connecting strap is arranged and disposed to cross over the patient's shoulder between the first attachment site and the second attachment site. The surgical restraint is arranged and disposed to restrain the patient's arm against the patient's torso and removed from a surgical site.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are exemplary surgical restraints. Embodiments of the present disclosure, in comparison to surgical restraints not utilizing one or more features disclosed herein, increases patient safety, decreases occlusion of a patient's arm into a surgical field, increases patient comfort, or combinations thereof.

Figure 1:
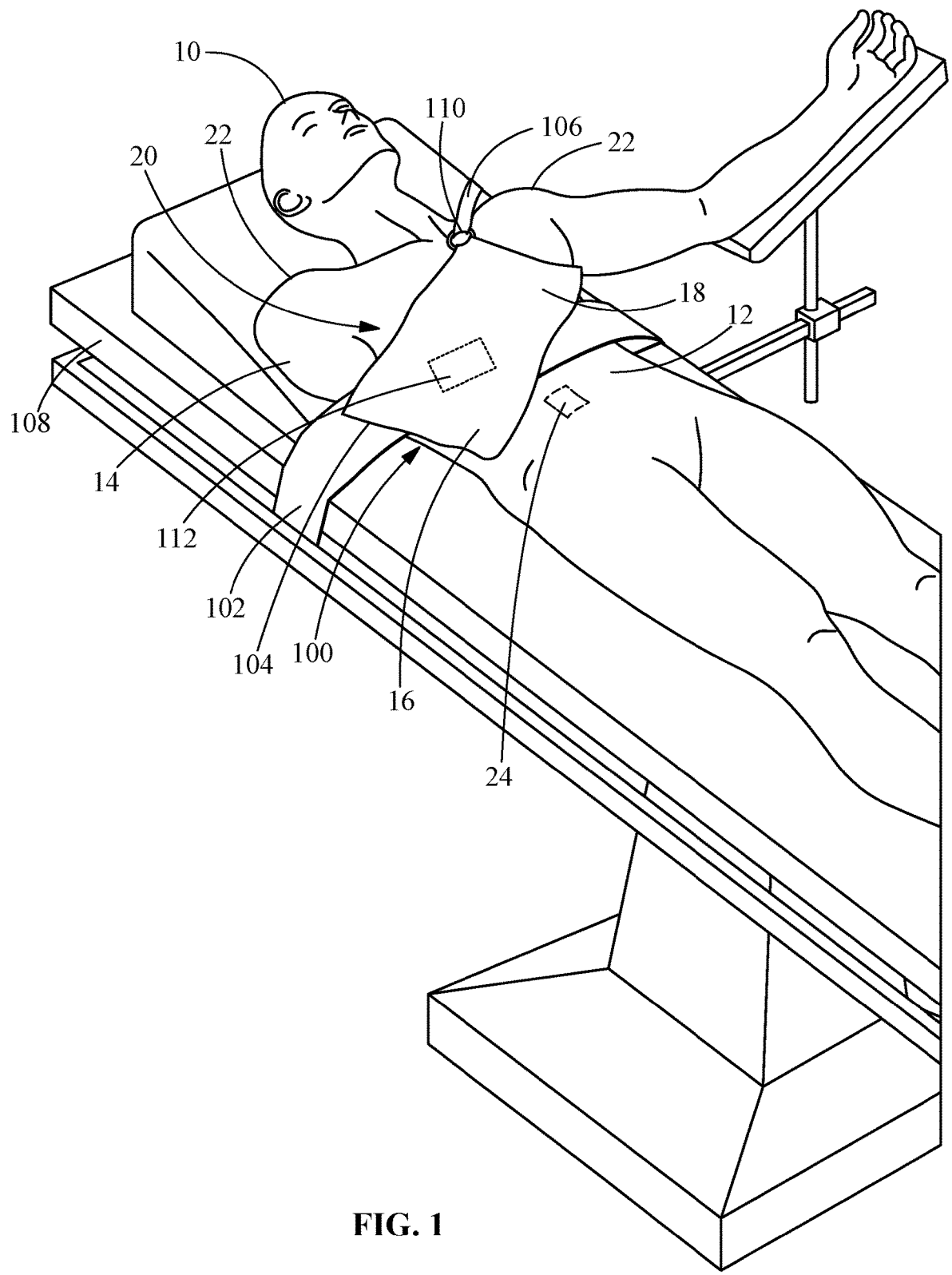
FIG. 1 is a left perspective view of a surgical restraint on a patient, according to an embodiment of the present disclosure.
Figure 2:
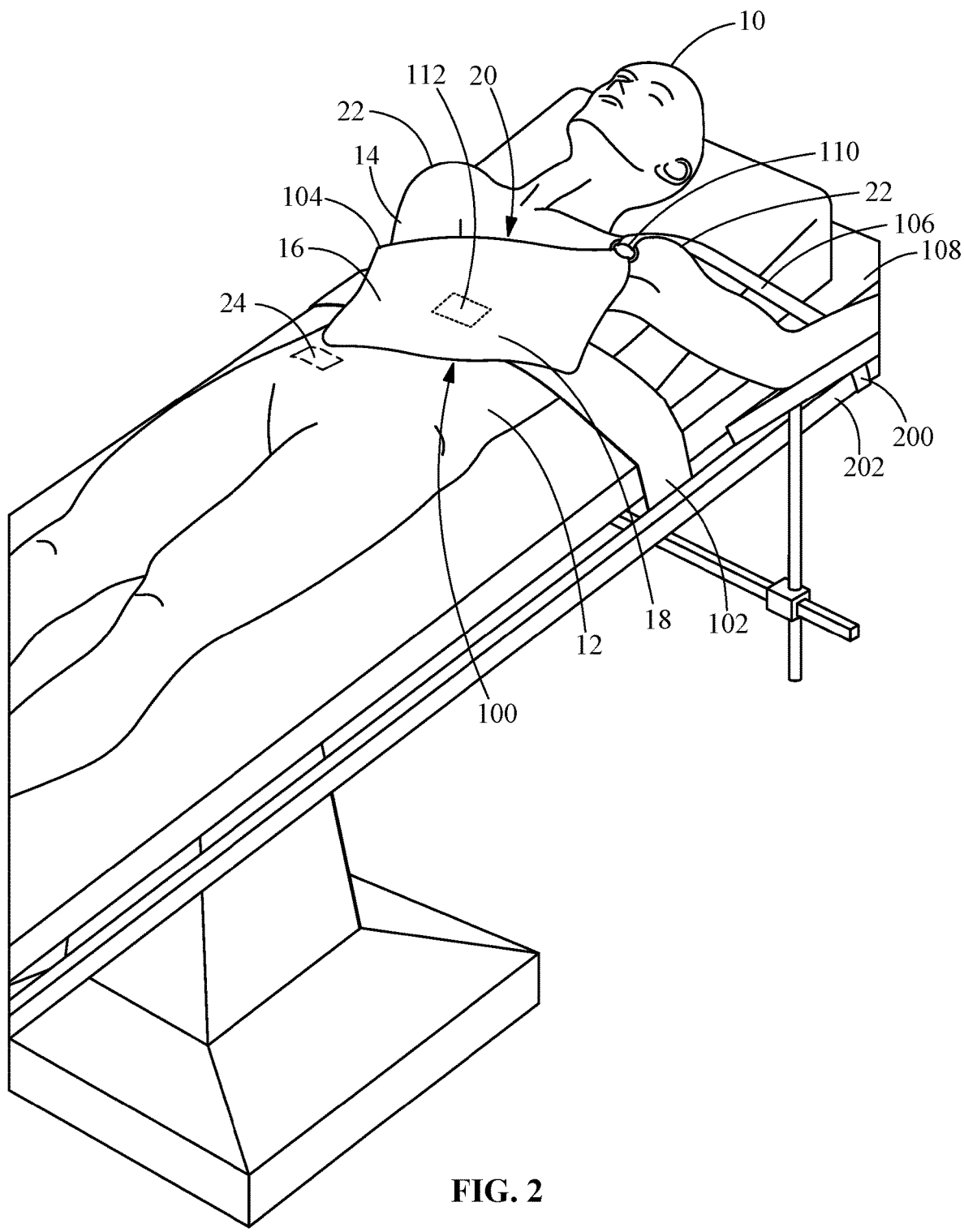
FIG. 2 is a right perspective view of the surgical restraint of FIG. 1, according to an embodiment of the present disclosure.

Referring to FIGS. 1 and 2, in one embodiment, a surgical restraint 100 includes a body strap 102, a sling 104, and a connecting strap 106. The body strap 102 is arranged and disposed to wrap over a torso 12 of a patient 10 and around a support 108 disposed below the patient 10, restraining the patient 10 against the support 108. The sling 104 is arranged and disposed to cradle an upper arm 14, an elbow 16, and a forearm 18 of an arm 20 of a patient 10. The connecting strap 106 includes a first attachment site 200 associated with brace 202 and a second attachment site 110 associated with the sling 104. The connecting strap 106 is arranged and disposed to cross over the shoulder 22 of the patient 10 between the first attachment site 200 and the second attachment site 110. The surgical restraint 100 is arranged and disposed to restrain the arm 20 of the patient 10 against the torso 12 of the patient 10 and removed from a surgical site 24.

The surgical restraint 100 may provide for the safe positioning of the arm 20, while protecting the arm 20, and holding the arm 20 away from the surgical site 24 during surgery while also providing a body strap 102 to keep the patient 10 positioned on an operating room table 108.

The surgical restraint 100 may have advantages over other non-inventive restraints, including, by way of example, that the surgical restraint 100 may be designed to position the arm 20 safely across the torso 12 during surgery. The surgical restraint 100 may be made from a fabric and may include protective padding. The surgical restraint 100 may be adjustable and cushioning in form to prevent injury to the patient 10 and prevent interference of the arm 20 or torso 12 position during surgery.

In one embodiment, the sling 104 envelopes the arm 20 holding it by the upper arm 14, elbow 16, and forearm 18. The sling 104 may be padded and cushioning. The sling 104 may be made of cloth, plastic, a paper material, or combinations thereof.

In one embodiment, the body strap 102 crosses the torso 12 perpendicularly, in order to hold down the patient 10 and also to hold the sling 104 in position. The body strap 102 may be cushioning. The body strap 102 may be made of cloth, plastic, a paper material, or combinations thereof.

Figure 3:
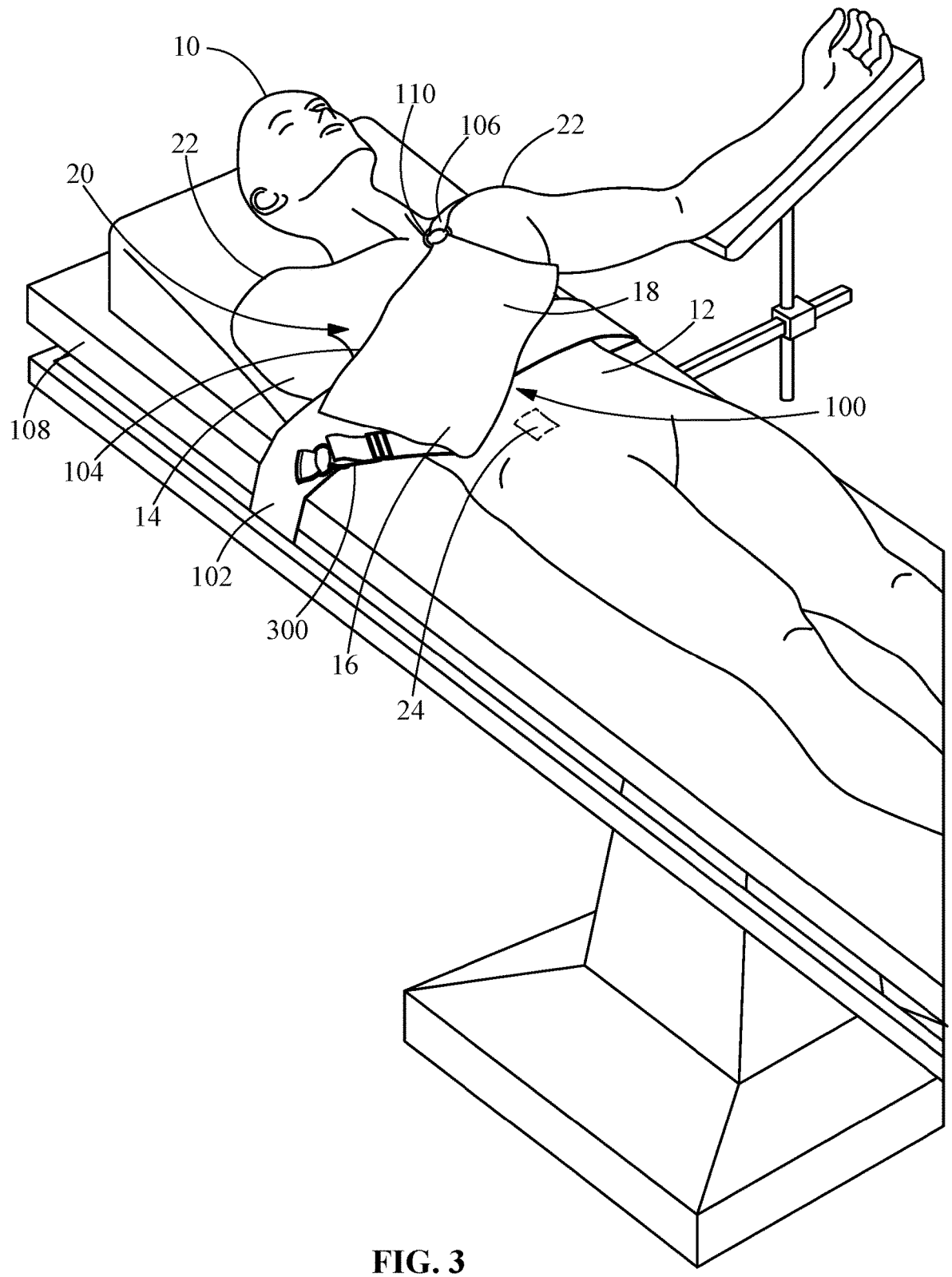
FIG. 3 is a right perspective view of the surgical restraint of FIG. 1 with adjustable straps, according to an embodiment of the present disclosure.
Figure 4:
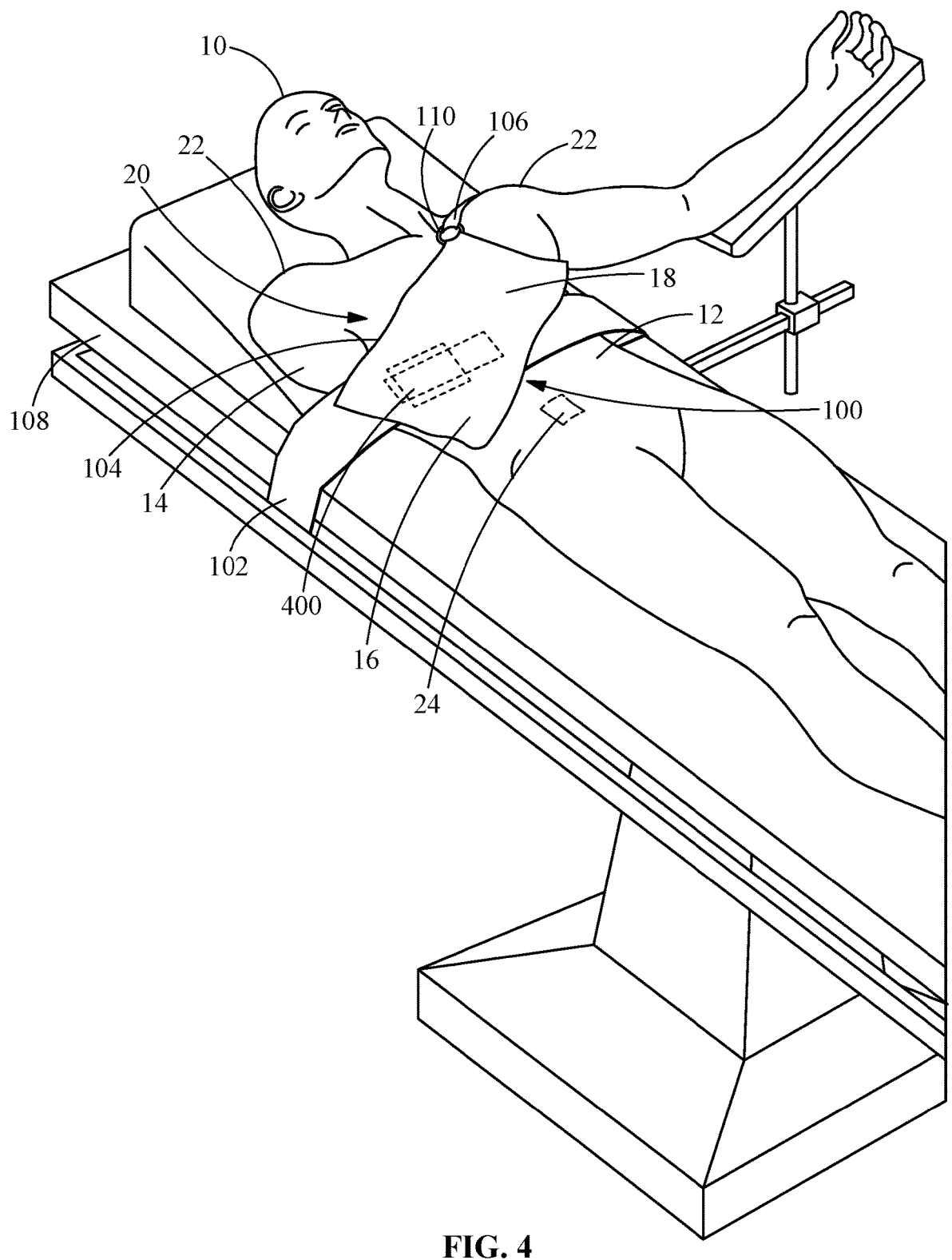
FIG. 4 is a right perspective view of the surgical restraint of FIG. 1 with hook and loop fasteners, according to an embodiment of the present disclosure.
Figure 5:
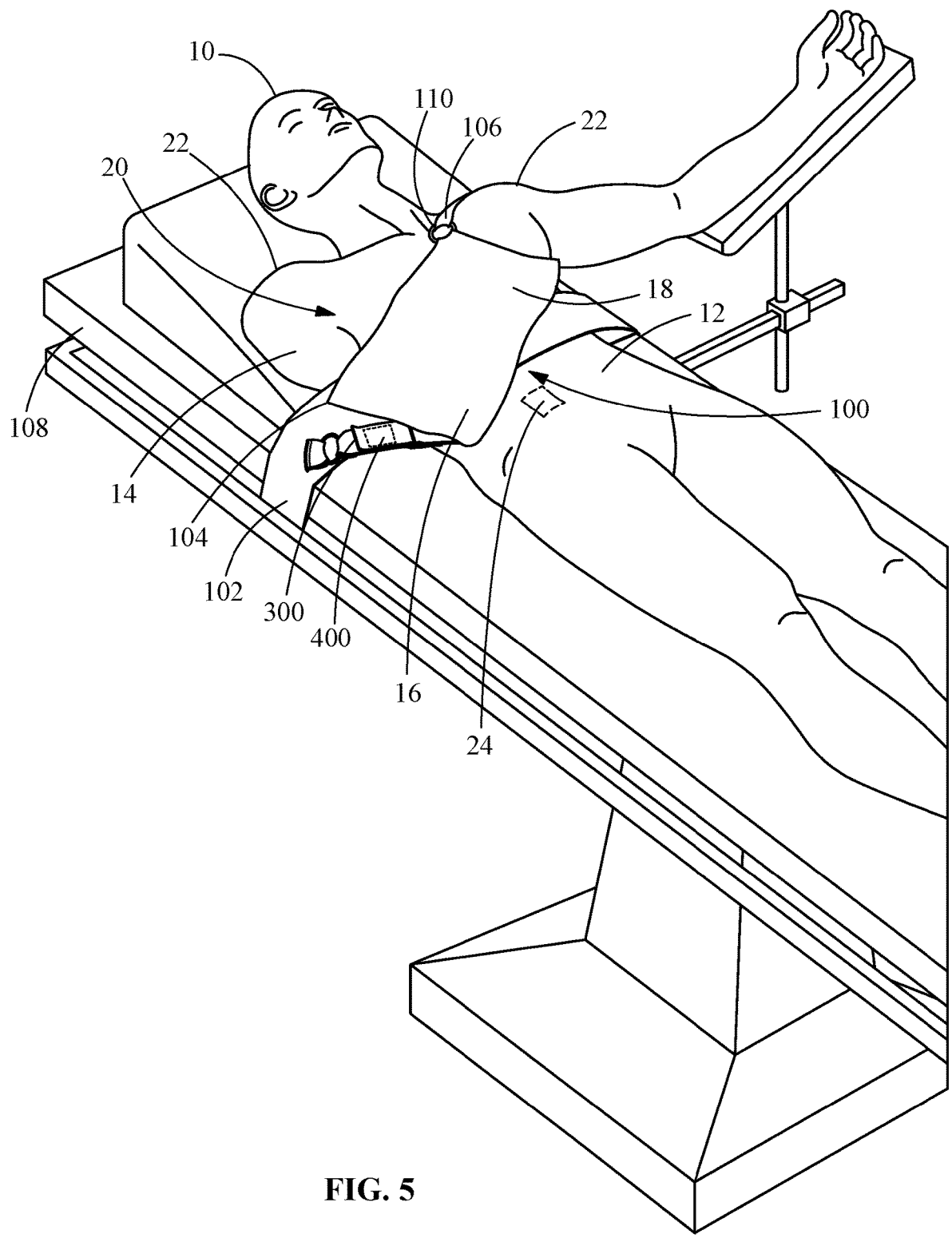
FIG. 5 is a right perspective view of the surgical restraint of FIG. 1 with adjustable straps having hook and loop fasteners, according to an embodiment of the present disclosure.

In one embodiment (FIGS. 1 and 2), the body strap 102 and the sling 104 are connected together using a permanent connection such as a textile stitching 112 or an adhesive. In another embodiment (FIGS. 3-5), the body strap 102 and the sling 104 are adjustably and/or releasably connected together. Adjustable and/or releasable connection may allow for adjustable positioning of the arm 20. Adjustable and/or releasable connections of the body strap 102 and the sling 104 include, but are not limited to, adjustable straps 300 (FIG. 3), hook and loop fasteners 400 (FIG. 4) such as, but not limited to, VELCRO, and combinations thereof (FIG. 5).

In one embodiment, the connecting strap 106 is adjustable and/or releasable. The connecting strap 106 may provide additional force, pulling the arm 20 across the torso 12 and upward, away from the surgical site 24.

The surgical restraint 100 may provide safe positioning of the surgical side arm 20 and patient 10. In one embodiment, the surgical restraint 100 is padded to protect the ulnar and other nerves. The surgical restraint 100 may be padded to protect the arm 20 from movements during surgery or from damaging contact with surgical objects such as a mallet or other instruments.

The body strap 102 may protect the patient 10 and keep the patient 10 positioned on a surgical bed 108.

The surgical restraint 100 may hold an arm 20 up and out of the way of the surgical site 24 towards the opposite side of the torso 12. In one embodiment, the sling 104 holds the surgery-side arm 20 up and out of the way of the surgical site 24.

The body 102 strap may be padded. In one embodiment, the body strap 102 attaches to a bed or a bed rail as the support 108. Attachment to the bed or the bed rail may be adjustable and/or releasable, and may be via a hook, strap around the rail, adhesive, clip, or any other suitable attachment arrangement. In one embodiment, fixation to the bed or the bed rail may be via three points: two directly opposite each other on below the arms 20, and one above the opposite shoulder 22 from the surgical site 24.

The connecting strap 106 may provide security to the arm 20 by pulling the arm 20 across the torso 12 to a safe, out-of-the-way position.

The surgical restraint 100 may provide padding of the torso 12 and arm 20.

In one embodiment, a brace is the support 108 or a portion of the support 108, such as, but not limited to, a bed or a bed rail. In another embodiment, the brace is the body strap 102 or a portion of the body strap 102. The connecting strap 106 may secure the arm 20 via the sling 104 to the bed or the bed rail as the support 108 or portion of the support 108. The connecting strap 106 may be releasable and/or adjustable and may be attached to the body strap 102 or the sling 104 by direct stitching, through a loop of fabric, through a metal or plastic ring arranged and disposed for multi directional connection to a bed or a bed rail, by a combination thereof, or by any other suitable mechanism. The connecting strap 106 may be oriented in any of a variety of directions to safely position the arm 20 including, but not limited to, above/superior to the opposite shoulder 22, below/inferior to the opposite shoulder 20, attached on the same side as the arm 20 or above/superior to the arm 20 on the same side of the bed or the bed rail as the support 108 or portion of the support 108 (i.e. surgical side), or combinations thereof.

The surgical restraint 100 may be securely connected to the bed or the bed rail as the support 108 or portion of the support 108 by a permanent and/or a releasable and/or adjustable arrangement, including, but not limited to, a hook and loop fastener such as, but not limited to, VELCRO, a locking clip, an adhesive bond, or combinations thereof.

The connecting strap may be securely connected to the sling and/or the brace by a permanent and/or a releasable and/or adjustable arrangement, including, but not limited to, a hook and loop fastener such as, but not limited to, VELCRO, a locking clip, an adhesive bond, or combinations thereof.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. All features described above in isolation are understood and intended to be combinable with one another in various combinations as would be understood by a person having ordinary skill in the art, unless specified to the contrary.

What is claimed is:

1. A surgical restraint comprising:
   a body strap arranged and disposed to wrap over an anterior surface of a torso of a patient disposed in a supine position and around a support disposed posterior to the patient, restraining the patient against the support;
   a sling attached to the body strap and arranged and disposed to cradle an upper arm, an elbow and a forearm of an arm of the patient with the sling disposed across the anterior surface of the torso from a first lateral side of the patient from which the arm extends and toward an opposing lateral side of the patient and with the torso being disposed between the sling and the support; and
   a connecting strap including a first attachment site associated with a brace and a second attachment site associated with the sling, the connecting strap being arranged and disposed to cross over a shoulder of the patient on the opposing lateral side between the first attachment site and the second attachment site and to pull the second attachment site toward the shoulder of the patient on the opposing lateral side,
   wherein the brace is the body strap or a portion of the body strap,
   wherein the surgical restraint is arranged and disposed to restrain the arm of the patient across and against the anterior surface of the torso while pulling the arm toward the shoulder of the patient on the opposing lateral side such that the arm is removed from and superior to a surgical site, and
   wherein the support is a surgical bed or an operating table or a portion of the surgical bed or the operating table.

2. The surgical restraint of claim 1, wherein the sling is directly attached to the body strap.

3. The surgical restraint of claim 2, wherein the sling is permanently attached to the body strap.

4. The surgical restraint of claim 2, wherein the sling is adjustably attached to the body strap.

5. The surgical restraint of claim 2, wherein the sling is releasably attached to the body strap.

6. The surgical restraint of claim 1, wherein the sling is permanently attached to the body strap.

7. The surgical restraint of claim 1, wherein the sling is adjustably attached to the body strap.

8. The surgical restraint of claim 1, wherein the sling is releasably attached to the body strap.

9. The surgical restraint of claim 1, wherein the sling is attached to the body strap by a hook and loop fastener.

10. The surgical restraint of claim 1, wherein the sling is attached to the body strap by an adjustable strap.

11. The surgical restraint of claim 1, wherein the portion of the surgical bed is a bed rail.

12. The surgical restraint of claim 1, wherein the connecting strap is adjustably attached to the brace at the first attachment site.

13. The surgical restraint of claim 1, wherein the connecting strap is releasably attached to the brace at the first attachment site.

14. The surgical restraint of claim 1, wherein the connecting strap is adjustably attached to the sling at the second attachment site.

15. The surgical restraint of claim 1, wherein the connecting strap is releasably attached to the sling at the second attachment site.

16. The surgical restraint of claim 1, wherein the connecting strap is arranged and disposed to exert a force toward the brace on the sling away from the surgical site.

17. A surgical restraint comprising:
a body strap arranged and disposed to wrap over an anterior surface of a torso of a patient disposed in a supine position and around a support disposed posterior to the patient, restraining the patient against the support;
a sling attached to the body strap and arranged and disposed to cradle an upper arm, an elbow and a forearm of an arm of the patient with the sling disposed across the anterior surface of the torso from a first lateral side of the patient from which the arm extends and toward an opposing lateral side of the patient and with the torso being disposed between the sling and the support; and
a connecting strap including a first attachment site associated with a brace and a second attachment site associated with the sling, the connecting strap being arranged and disposed to cross over a shoulder of the patient on the opposing lateral side between the first attachment site and the second attachment site and to pull the second attachment site toward the shoulder of the patient on the opposing lateral side,
wherein the brace is the support or a portion of the support,
wherein the surgical restraint is arranged and disposed to restrain the arm of the patient across and against the anterior surface of the torso while pulling the arm toward the shoulder of the patient on the opposing lateral side such that the arm is removed from and superior to a surgical site, and
wherein the support is a surgical bed or an operating table or a portion of the surgical bed or the operating table.

* * * * *